(12) United States Patent
Bhadra et al.

(10) Patent No.: US 11,957,469 B2
(45) Date of Patent: Apr. 16, 2024

(54) MODIFIED NERVE CUFF ELECTRODE DESIGN FOR STABLE RECORDING AND/OR STIMULATION

(71) Applicant: Case Western Reserve University, Cleveland, OH (US)

(72) Inventors: Narendra Bhadra, Cleveland, OH (US); Tina L. Vrabec, Cleveland, OH (US); Niloy Bhadra, Cleveland, OH (US); Kevin L Kilgore, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 558 days.

(21) Appl. No.: 16/652,692

(22) PCT Filed: Oct. 2, 2018

(86) PCT No.: PCT/US2018/053843
§ 371 (c)(1),
(2) Date: Apr. 1, 2020

(87) PCT Pub. No.: WO2019/070625
PCT Pub. Date: Apr. 11, 2019

(65) Prior Publication Data
US 2020/0345255 A1    Nov. 5, 2020

Related U.S. Application Data

(60) Provisional application No. 62/634,906, filed on Feb. 25, 2018, provisional application No. 62/566,849, filed on Oct. 2, 2017.

(51) Int. Cl.
*A61B 5/00* (2006.01)
*A61B 5/24* (2021.01)
*A61N 1/05* (2006.01)

(52) U.S. Cl.
CPC .............. *A61B 5/24* (2021.01); *A61N 1/0556* (2013.01)

(58) Field of Classification Search
None
See application file for complete search history.

(56) References Cited

U.S. PATENT DOCUMENTS

| | | | |
|---|---|---|---|
| 6,259,938 B1 * | 7/2001 | Zarychta | A61B 5/6856 604/528 |
| 7,536,227 B1 * | 5/2009 | Poore | A61B 5/0538 600/377 |

(Continued)

FOREIGN PATENT DOCUMENTS

| | | |
|---|---|---|
| AU | 2015330072 A1 | 4/2017 |
| WO | 2007/140597 A1 | 12/2007 |
| WO | 2008/039982 A2 | 4/2008 |

OTHER PUBLICATIONS

Foldes, Emily L., et al. "Design, fabrication and evaluation of a conforming circumpolar peripheral nerve cuff electrode for acute experimental use." Journal of neuroscience methods 196.1 (2011): 31-37.

(Continued)

*Primary Examiner* — John R Downey
*Assistant Examiner* — Anant A Gupta
(74) *Attorney, Agent, or Firm* — TAROLLI, SUNDHEIM, COVELL & TUMMINO, LLP

(57) ABSTRACT

A modified nerve cuff electrode is designed to enhance the stability of neural recording and/or nerve stimulation. Any nerve cuff electrode includes a nerve cuff and a plurality of electrodes within the nerve cuff. While traditional nerve cuff electrodes have every one of the plurality of electrode contacts on the inner surface of the nerve cuff, in the modified nerve cuff electrode each of an inner surface and an outer surface of the nerve cuff has at least one electrode (Continued)

contact. The at least one electrode contact on the outer surface can be electrically isolated from the peripheral nerve to provide a stable reference or ground during recording or a stable pathway for a return current during stimulation to enhance the stability of the recording or the stimulation.

8 Claims, 7 Drawing Sheets

(56) References Cited

U.S. PATENT DOCUMENTS

| | | | |
|---|---|---|---|
| 2004/0015204 A1 | 1/2004 | Whitehurst et al. | |
| 2005/0010265 A1* | 1/2005 | Baru Fassio | A61N 1/36067 |
| | | | 607/48 |
| 2008/0172116 A1* | 7/2008 | Mrva | A61N 1/0526 |
| | | | 607/115 |
| 2010/0042186 A1* | 2/2010 | Ben-David | A61B 5/4041 |
| | | | 607/118 |
| 2010/0161019 A1 | 6/2010 | Clark et al. | |
| 2012/0150255 A1 | 6/2012 | Lindenthaler et al. | |
| 2013/0150940 A1 | 6/2013 | Wilson et al. | |
| 2014/0046407 A1 | 2/2014 | Ben-Ezra et al. | |
| 2017/0202467 A1* | 7/2017 | Zitnik | A61N 1/3756 |
| 2018/0117313 A1* | 5/2018 | Schmidt | A61N 1/3752 |

OTHER PUBLICATIONS

PCT International Search Report and Written Opinion for corresponding International Application Serial No. PCT/US2018/053843, dated Nov. 26, 2018, pp. 1-15.

* cited by examiner

MODIFIED NERVE CUFF ELECTRODE DESIGN FOR STABLE RECORDING AND/OR STIMULATION

RELATED APPLICATIONS

This application claims the benefit of U.S. Provisional Application No. 62/566,849, filed Oct. 2, 2017, entitled "NERVE CUFF ELECTRODE DESIGN AND FABRICATION WITH OBVERSE AND REVERSE CONTACT WINDOWS." This application also claims the benefit of U.S. Provisional Application No. 62/634,906, filed Feb. 25, 2018, entitled "MODIFIED NERVE CUFF DESIGN AND FABRICATION METHOD FOR STABLE RECORDING AND/OR STIMULATION." The entireties of these applications is hereby incorporated by reference for all purposes.

GOVERNMENT SUPPORT

This invention was made with government support under R01-NS-074149 awarded by the National Institutes of Health (NIH) National Institute of Neurological Disorders and Stroke (NINDS). The government has certain rights in the invention.

TECHNICAL FIELD

The present disclosure relates generally to neural recording and/or stimulation and, more specifically, to a modified nerve cuff electrode design that enables stable neural recording and/or stimulation.

BACKGROUND

A nerve cuff electrode, which include a nerve cuff with one or more electrical contacts on the interior surface of the nerve cuff, can be used for neural recording and/or stimulation applications. To facilitate the neural recording and/or stimulation applications, such nerve cuff electrodes also require the use of a remote ground or return electrode that is placed within a subject's tissue when the nerve cuff electrode is wrapped around the subject's nerve. Use of a remote ground or return electrode within the subject's tissue can lead to poor repeatability between experiments. For example, the position of the remote ground or return electrode may vary between experiments due to differences in surgical procedure and in local anatomy. The remote ground or return electrode also introduces unique artifacts, like movement artifacts, which can lead to additional variation. Such instability and irreproducibility lead to poor neural recording and/or stimulation applications.

SUMMARY

The present disclosure relates generally neural recording and/or stimulation and, more specifically, to a modified nerve cuff electrode design that enables stable recording and/or stimulation. The stable recording and/or stimulation provided by the modified nerve cuff electrode design also can be highly reproducible.

In one aspect, the present disclosure can include a nerve cuff electrode designed to enhance stability of neural recording and/or stimulation. The nerve cuff electrode includes a plurality of electrode contacts and a nerve cuff. The nerve cuff includes an inner surface with at least one of the plurality of electrode contacts and an outer surface with at least one other of the plurality of electrode contacts. The at least one electrode contact on the inner surface can be configured to make electrical contact with a peripheral nerve. The other at least one electrode contact on the outer surface can be a reverse-facing electrode contact that can be configured to be electrically isolated from the peripheral nerve.

In another aspect, the present disclosure can include a method for using a nerve cuff electrode with a modified design that includes a nerve cuff with an inner surface with at least one electrical contact that contacts a peripheral nerve and an outer surface with at least one reverse-facing electrical contact that is electrically isolated from the peripheral nerve. The nerve cuff electrode can be applied around at least a portion of the peripheral nerve. The at least one electrode contact of the inner surface and the at least one reverse-facing electrode contact of the outer surface are each configured to be placed in electrical contact with a lead wire that is operatively coupled to an external device, which is configured for recording and/or stimulation. Accordingly, the nerve cuff can be used to record activity from the peripheral nerve and/or stimulate the peripheral nerve by delivering an electrical signal to the peripheral nerve.

In a further aspect, the present disclosure can include a method for fabricating a nerve cuff electrode. The method includes inserting at least two electrode contacts between a first insulative layer and a second insulative layer. Then a first contact window is formed in the first insulative layer over one of the at least two electrode contacts. A second contact window is then formed in the second insulative layer over another of the at least two electrode contacts. The first insulative layer and the second insulative layer are then shaped to form a cuff.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
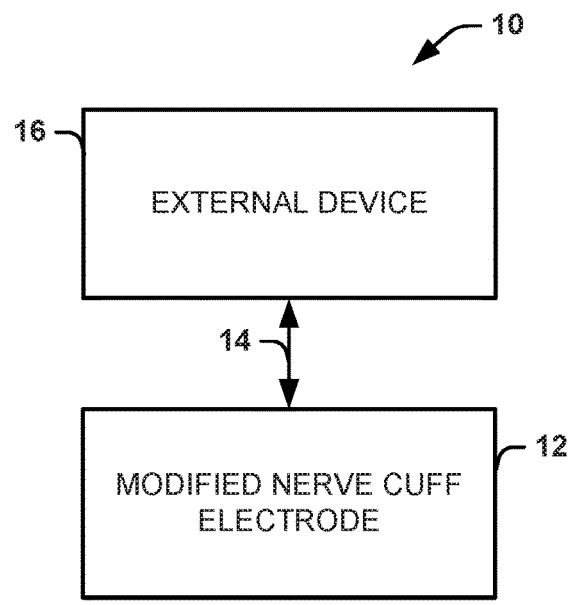
FIG. 1 is a block diagram illustration showing an example of a system for neural recording and/or stimulation of peripheral nerves in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "nerve cuff electrode" refers to an implantable device made of a nerve cuff and one or more electrical contacts. The nerve cuff electrode can be configured for neural recording and/or stimulation.

As used herein, the term "nerve cuff" refers to an implantable device that has a cylindrical geometry to conform to the shape of a nerve and encircle the nerve.

As used herein, the term "inner surface" refers to a surface of a nerve cuff that faces toward a nerve when the nerve cuff is placed around the nerve and at least partially encircles the nerve. The term "obverse surface" can be used interchangeably with "inner surface".

As used herein, the term "outer surface" refers to a surface of a nerve cuff that faces away from the nerve when the nerve cuff is placed around the nerve and at least partially encircles the nerve. The term "reverse surface" can be used interchangeably with "outer surface". For example, an element that is "reverse facing" is on the outer surface of the nerve cuff.

As used herein, the term "electrical contact" refers to an electrical conductor that can provide current to and/or receive current from a nerve. The term "electrode contact" can be used interchangeably with "electrical contact".

As used herein, the term "electrical isolation" refers to a state where one electrical conductor or group of electrical conductors is unable to send or receive current to or from another electrical conductor or group of electrical conductors. For example, electrically isolated conductors can be separated by an insulative material.

As used herein, the term "insulative" refers to a type of material through which virtually no (or very little current) flows.

As used herein, the term "peripheral nervous system" refers to the nervous system outside the brain and spinal cord.

As used herein, the term "nerve" refers to a component of the peripheral nervous system that transmits information between body parts (e.g., between the brain and/or spinal cord and one or more peripheral organs). A nerve can include a bundle of nerve fibers, which can include motor, sensory, and/or autonomic fibers.

As used herein, the term "stable" when used with recording or stimulation refers to a neural recording or stimulation that is repeatable regardless of different operating conditions.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "operatively coupled" can refer to a state of attachment between two or more components to enable the transfer of data. The attachment can be wired and/or wireless.

II. Overview

The present disclosure relates generally to neural recording and/or stimulation and, more particularly, to a modified nerve cuff electrode design that enables stable recording and/or stimulation. The modified nerve cuff electrode design includes a nerve cuff with an inner surface with one or more electrode contacts and an outer surface with at least one reverse-facing electrode contact facing away from the nerve. Traditional nerve cuffs electrodes employ the one or more contacts on the inner surface, but require the use of a separate ground or return electrode that is placed within the subject's body remote from the nerve cuff. The recording and/or stimulation achieved using the modified nerve cuff electrode can be far more stable than the recording and/or stimulation achieved using a traditional nerve cuff electrode. The present disclosure also relates to a modified fabrication method for creating nerve cuff electrodes of the modified design with the one or more reverse-facing contacts on the outer side of the nerve cuff.

III. Systems

One aspect of the present disclosure can include a system 10 (FIG. 1) for neural recording and/or stimulation of peripheral nerves. The system 10 can employ a modified nerve cuff electrode 12 with at least one simple reverse-facing electrode contact that does not make direct electrical connection with the nerve. By using the modified nerve cuff electrode 12, the system 10 can achieve stable recording and/or stimulation that are inconceivable using traditional nerve cuff electrodes with remote ground or return electrodes. As an example, when the modified nerve cuff electrode 12 is used for recording, a single reverse-facing electrode contact can be configured to act as a ground contact; however, when the modified nerve cuff electrode 12 is used for stimulation, two reverse-facing electrode contacts can be configured to act as a pathway for return current.

The system 10 can include the modified nerve cuff electrode 12 operatively coupled to an external device 16. As illustrated, the operative coupling can occur by a lead wire 14. The lead wire 14 can include a bundle of individual wires connected to the modified nerve cuff electrode 12. However, in some instances, the operative coupling can be at least partially wireless. The external device 16 can include circuitry configured to communicate with the modified nerve cuff electrode 12. The external device 16 can, in some instances, receive and display neural recordings from a peripheral nerve. In other instances, the external device 16 can configure electrical stimulations to be delivered to the peripheral nerve. In still other instances, the external device 16 can be configured for both stimulation and recording.

The modified nerve cuff electrode 12 can include a nerve cuff and a plurality of electrical contacts. The nerve cuff can have an inner surface, which includes one or more electrical contacts, and an outer surface that includes an additional one or more electrical contacts. The inner surface defines an inner diameter of the nerve cuff that is equal to at least the diameter of the peripheral nerve. Notably, the one or more electrical contacts on the outer surface are electrically isolated from the one or more electrical contacts on the inner surface. An example of the modified nerve cuff electrode 12 is shown in greater detail in FIG. 2.

Figure 2:
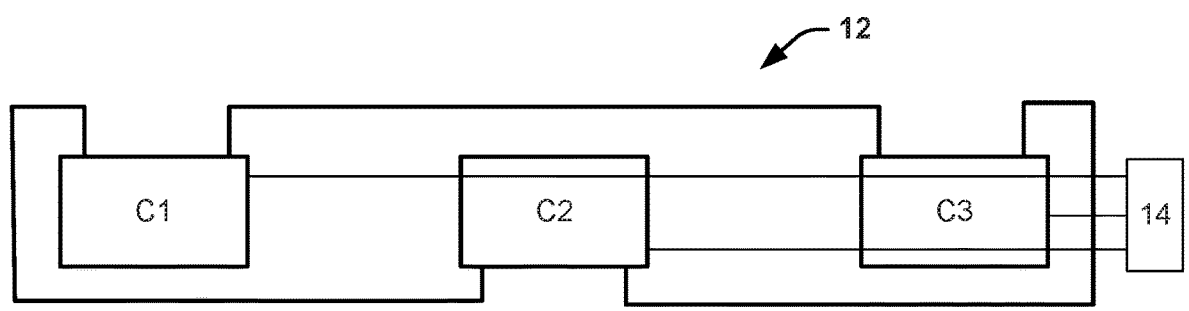
FIG. 2 is a block diagram illustration showing the modified nerve cuff electrode of FIG. 1 in greater detail.

In FIG. 2, the modified nerve cuff electrode 12 is shown as a tripolar electrode with three electrical contacts (C1, C2, C3)—two electrical contacts (C1 and C3) on one side of the cuff (either the inner surface or the outer surface) and one electrical contact (C2) on the other side of the cuff (the opposite of either the inner surface or the outer surface). Although three electrode contacts (C1, C2, C3) are shown in FIG. 2, it will be understood that the number of electrode contacts is not limited to three. Various conductive materials can be used for construction of the electrical contacts (C1, C2, C3), including platinum, iridium, stainless steel, and/or any other type of conductive material or combination of conductive material, like an alloy, that is biocompatible chosen based on the application or use of the nerve cuff. The nerve cuff can be constructed from an insulating material, like silicone rubber, Teflon, or the like.

As shown, each of the three electrical contacts (C1, C2, C3) are operatively coupled to the external device 16 through individual component wires, which are bundled together to form the lead wire 14. In other words, each of the electrical contacts (C1, C2, C3) can be placed in electrical contact with an individual component wire of the lead wire 14. The individual component wires can be made of any biocompatible, conductive material, like stainless steel. In some instances, the lead wire 14 may be clad at least in part by a biocompatible material. Although not illustrated, the operative coupling can be, at least in part, wireless.

The modified nerve cuff electrode 12 can be configured for recording activity from a peripheral nerve and/or stimulation of the peripheral nerve. When the modified nerve cuff electrode 12 is configured for recording, the inner surface of the nerve cuff can include two electrical contacts (C1 and C3) and the outer surface of the nerve cuff can include a single reverse-facing electrical contact (C2) located between electrical contacts (C1 and C3). The two electrical contacts (C1 and C3) on the inner surface are configured for recording activity of the peripheral nerve. The one electrical contact on the outer surface is configured to provide a stable reference or ground during the recording.

When the modified nerve cuff electrode 12 is configured for stimulating the peripheral nerve, the inner surface of the nerve cuff can include a single electrical contact (C2) configured for delivering an electrical signal to the peripheral nerve. In other words, the single electrical contact (C2) can be configured for monopolar stimulation. The outer surface of the nerve cuff can include two reverse-facing electrical contacts (C1 and C3) configured to provide a stable pathway for a return current. The single electrical contact (C2) can be located between the two reverse-facing electrical contacts (C1 and C3).

IV. Methods

Figure 3:
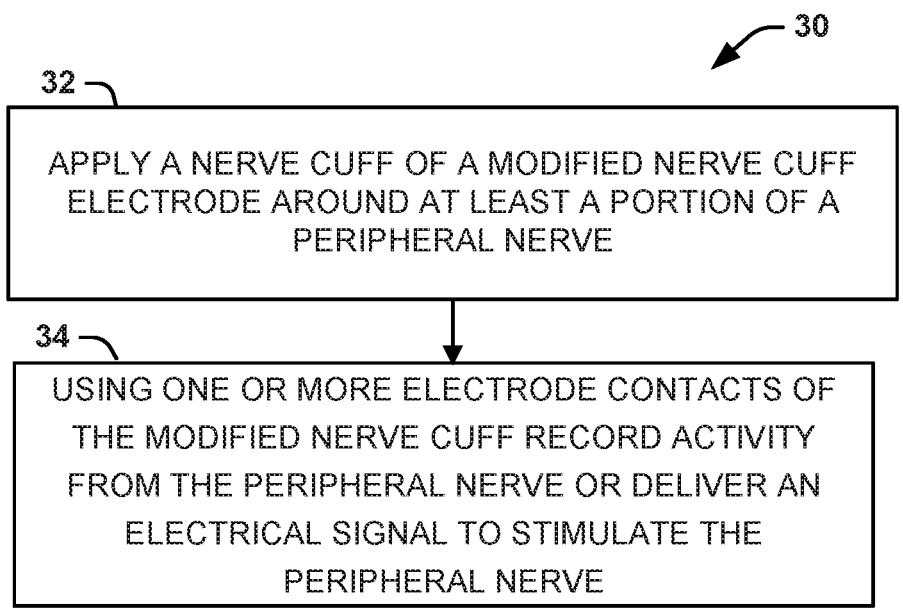
FIG. 3 is a process flow diagram of an example method for using the modified nerve cuff of FIG. 1 in accordance with another aspect of the present disclosure.
Figure 4:
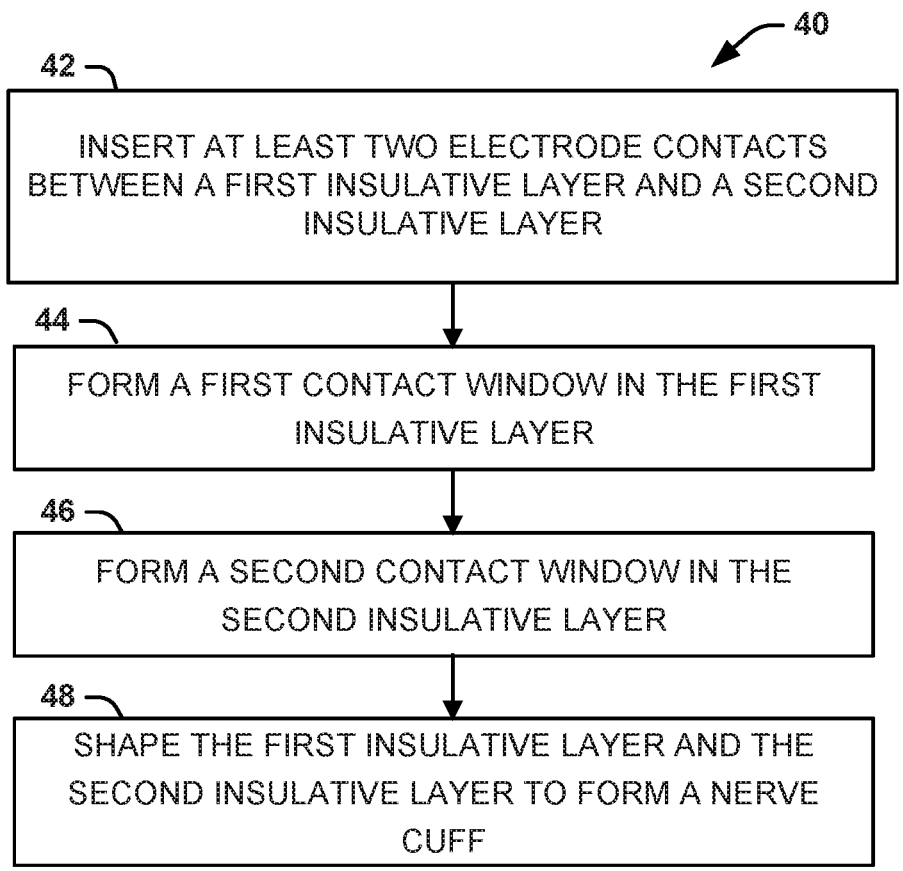
FIG. 4 is a process flow diagram of an example method for constructing the modified nerve cuff of FIG. 1 in accordance with a further aspect of the present disclosure.

Another aspect of the present disclosure can include methods 30, 40 for making and using the modified nerve cuff electrode 12. FIG. 3 shows a method 30 for using the modified nerve cuff electrode 12. FIG. 4 shows a method 40 for constructing the modified nerve cuff electrode 12. The methods 30 and 40 are illustrated as process flow diagrams with flowchart illustrations. For purposes of simplicity, the methods 30 and 40 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30 and 40.

Referring now to FIG. 3, illustrated is a method 30 for using the modified nerve cuff electrode 12. As shown in FIG. 1, the modified nerve cuff electrode 12 can be connected to an external device 16 by a lead wire 14. As shown in FIG. 2, the modified nerve cuff electrode 12 can have at least one reverse-facing electrode contact and at least one internal electrode contact. As step 32, a nerve cuff of the modified nerve cuff electrode 12 can be applied around at least a portion of a peripheral nerve. Depending on the application—recording or stimulation—the electrode contacts cam be arranged differently on the inner and outer side of the nerve cuff. At step 34, depending on configuration of the modified nerve cuff electrode 12 and functionality of the external device 16, activity from the peripheral nerve can be recorded or an electrical signal can be delivered to stimulate the peripheral nerve by the one or more electrode contacts on the inner surface of the nerve cuff. The at least one reverse-facing electrode contact can provide a stable reference or ground during the recording and/or a stable pathways for a return current due to the delivering. The reverse-facing one or more electrode contacts lead to a stability not seen with traditional nerve cuff electrodes that require an external electrode reference, ground, or return pathway.

Referring now to FIG. 4, illustrated is a method 40 for constructing the modified nerve cuff electrode 12. At step 42, at least two electrode contacts can be inserted between a first insulative layer and a second insulative layer. The electrode contacts can be made of one or more biocompatible conductive materials. For example, the electrode contacts can be platinum. At least one of the insulative layers can be made of one or more non-conductive materials, like silicone. The at least two electrode contacts can be electrically isolated from one another by the insulative layers. Electrical connections can be made between a lead wire and each of the at least two electrode contacts (in other words, separate wires of the lead wire can contact each of the electrode contacts).

At step 44, a first contact window can be formed in the first insulative layer. At 44, a second contact window can be formed in the second insulative layer. The first contact window can be over one of the electrode contacts, while the second contact window can be over another one of the electrode contacts, such that an active surface of the respective electrode contact is exposed. Each of the contact windows can be sized to dimensions of the respective one of the at least two electrode contacts. At 48, the first insulative layer and the second insulative layer can be shaped to form a nerve cuff. Depending on the application and the specific nerve being studied, the dimensions required to form the nerve cuff can be determined and the first insulative layer and the second insulative layer can be cut to fit the dimensions. For example, the inner diameter of the nerve cuff can be defined to be equal to at least the diameter of the peripheral nerve multiplied by pi.

V. Example Applications

Nerve cuff electrodes designed and fabricated as described herein can be used for neural recording and/or stimulation applications. These nerve cuff electrodes can be sized and dimensioned for use. For example, a nerve cuff electrode used with rat sciatic nerves can be of a different size than a nerve cuff electrode used with cat pudendal nerves. The following example applications are not meant to be exhaustive, but rather to give context as to potential uses of the nerve cuff electrodes designed and fabricated as designed herein.

Recording: A nerve cuff electrode of the present disclosure can include a nerve cuff fabricated with an inner surface, which includes two or more electrode contacts configured for recording activity of a peripheral nerve, and an outer surface that includes a single reverse-facing electrode contact configured to provide a stable reference or ground during recording that does not make contact with the nerve and is electrically isolated from the nerve. For example, the single reverse-facing electrode contact can be located between (in the middle of) the two or more electrode contacts on the inner surface. A potential application of the nerve cuff electrode configured for recording is found in the recording of compound action potentials (CAP) to monitor activity and study neural function. The single reverse-facing electrode contact provides a stable reference or ground for the CAP recordings.

Stimulation: A nerve cuff electrode of the present disclosure can include a nerve cuff fabricated with an inner surface, which includes a single electrode contact configured for delivering an electrical stimulation signal to a peripheral nerve, and an outer surface that includes two or more reverse-facing electrode contacts configured to provide a stable pathway for return current that do not make contact with the nerve and are electrically isolated from the nerve. For example, the single stimulation electrode on the inner surface contact can be located between (in the middle of) the two or more reverse facing return electrode contacts. A potential application of the nerve cuff electrode configured for stimulation is found in monopolar stimulation applications. The two or more reverse-facing return electrodes provide a stable pathway for the return current.

VI. Experimental

The following example is shown for the purpose of illustration only and is not intended to limit the scope of the appended claims. This example shows a modified nerve cuff electrode 12, which includes a reverse-facing, electrically isolated ground, used for stable compound action potential (CAP) recordings during experiments on rat sciatic nerves.

Materials and Methods

Design Features

Figure 5:
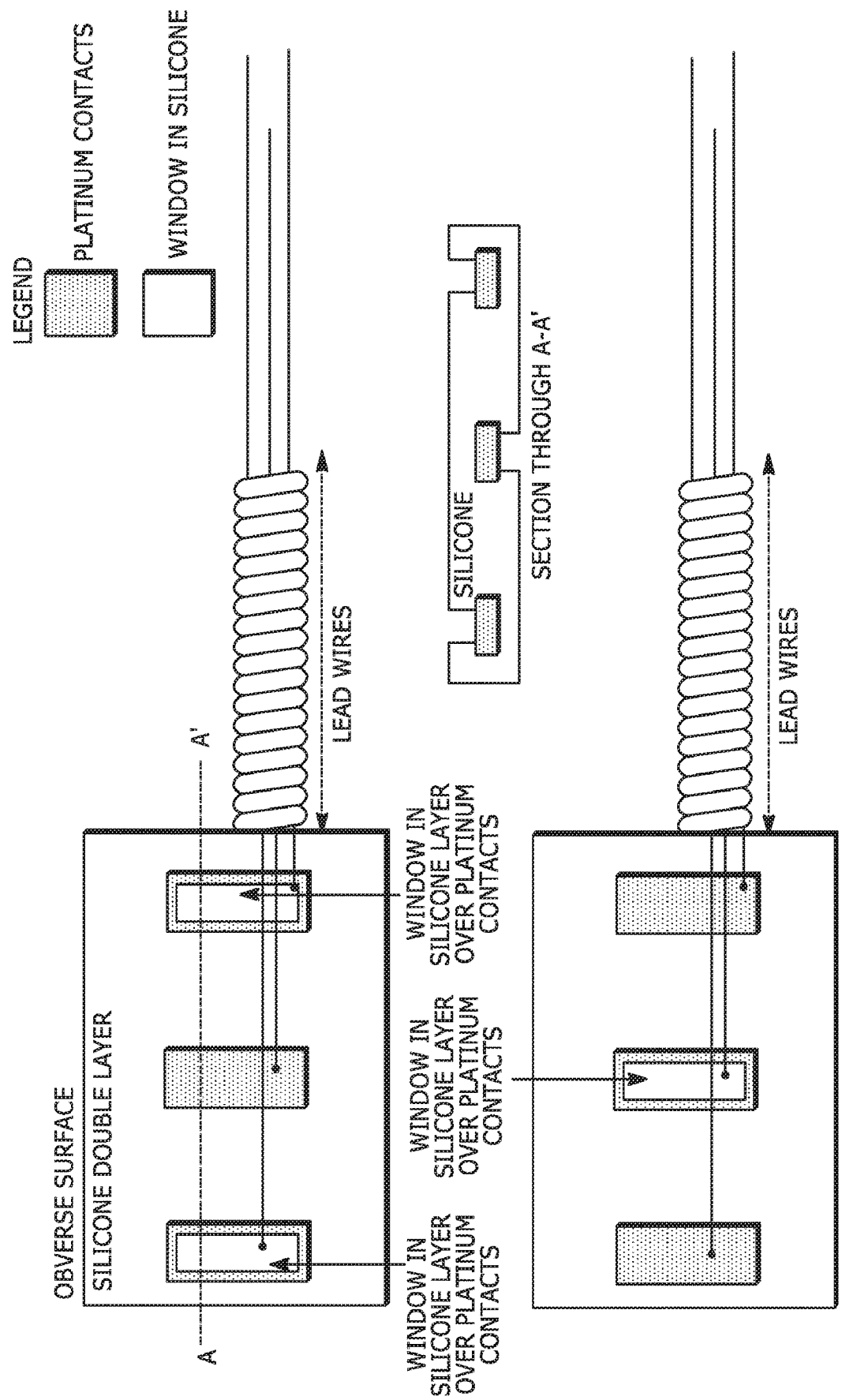
FIG. 5 is an illustration of an example of a tripolar nerve cuff with two flanking contacts for recording a Compound Action Potential (CAP) and a central reverse racing window to be connected as a ground.
Figure 6:
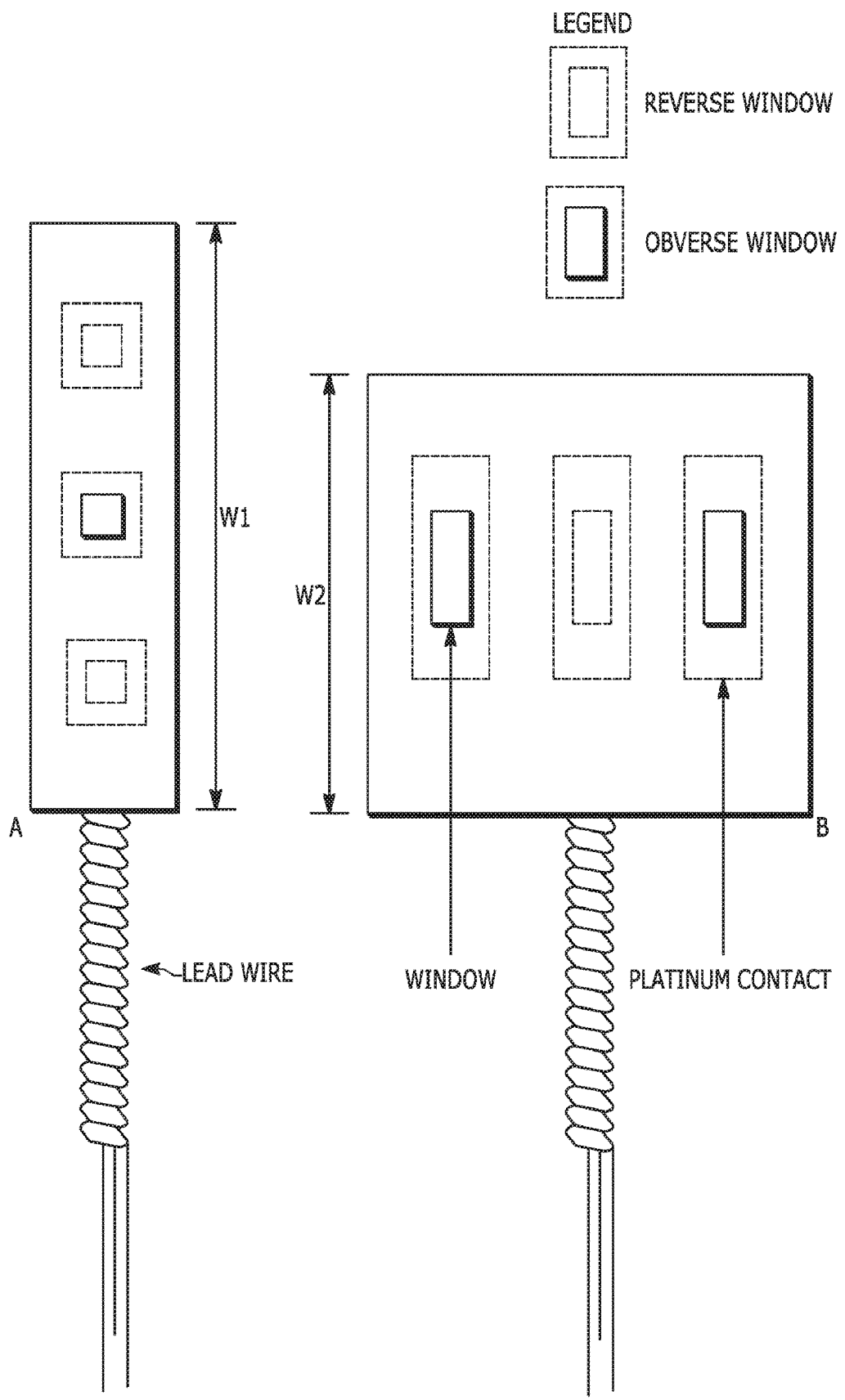
FIG. 6 is an illustration of two different tripolar electrode configurations.

The modified nerve cuff electrode 12 used for stable CAP recordings was designed for recording. The internal surface of the nerve cuff included bipolar recording contacts, while the external surface of the nerve cuff included a central ground (reference) electrode, as shown in FIG. 5. The distance between the recording contacts and the cuff diameter were determined based on the macro-anatomy of the target nerve. In other instances, however, the nerve cuff electrode may be designed for monopolar stimulation with a central contact facing the nerve and two flanking contacts facing the exterior of the nerve (FIG. 6, A showing contacts arrayed axially around the target nerve for monopolar stimulation and B with contacts arrayed in the longitudinal nerve axis. The cuff widths, w1 and w2, are greater than πd, where d is the nerve diameter).

Fabrication Steps

The modified nerve cuff electrodes were fabricated according to the following steps. The steps are derived from the fabrication method described in Foldes, E. L., et al. (2011) "Design, fabrication and evaluation of a conforming circumpolar peripheral nerve cuff electrode for acute experimental use". *J of Neurosci Methods:* 196(1), pp. 31-37.

Step 1: Electrode contacts were cut from 25 μm platinum foil (Alfa Aesar, Wood Hill, Mass.) individually with dimensions required by the target nerve.

Step 2: Teflon insulated stainless steel 250 μm diameter lead wires (Fort Wane Metal, Fort Wayne, Ind.) were used to form electrical connections to each intended electrode contact. The de-insulated tip of each lead wire was spot welded to its contact.

Step 3: The platinum contacts were laid between two layers of silicone sheeting, for molding the cuff. The two peripheral contacts were placed with the weld surface face down and the central contact with weld surface facing up. A very small amount of the adhesive silicone (MED-1511, NuSil Technology, Carpinteria, Calif.) was applied to the platinum contacts before positioning them over the bottom silicon sheeting to keep in position. The cuff was molded with two-part silicone elastomer (MED-4211, NuSil Technology, Carpinteria, Calif.; 100 degrees C. and 5,000 psi of pressure for 1 hour).

Step 4: Contact windows were carefully cut to the required dimensions using a sharp scalpel blade under magnification—two windows for the flanking recording contacts out of the top silicone sheet and one window for the central contact on the bottom silicon sheet. First, the contact windows were cut on the top silicone sheet, the molded silicone layers were peeled from the molding plates and flipped over on the molding plates, and the additional contact window was then incised on the reverse side.

Step 5: The silicone sheet surrounding the platinum electrode contacts was cut to the desired cuff dimensions.

Step 6: The electrode was wrapped around a stainless steel rod to give a cylindrical shape with known diameter.

In Vivo Experiment—Rat Sciatic Nerve

Reverse window bipolar nerve cuff electrodes with central reverse window (constructed as described above with an internal diameter of 1 mm) were implanted on the trunk of the Left Sciatic nerve in six Sprague Dawley (S-D) rats under Flurothane anesthesia. A small bipolar electrode was implanted proximally in each rat for stimulation. Single electrical pulses of varying pulse durations (20 μs to 10 ms) and increasing amplitudes were applied to the proximal electrode. CAPs were recorded from the sciatic nerve of each rat using the respective reverse window bipolar cuff.

Results

Figure 7:
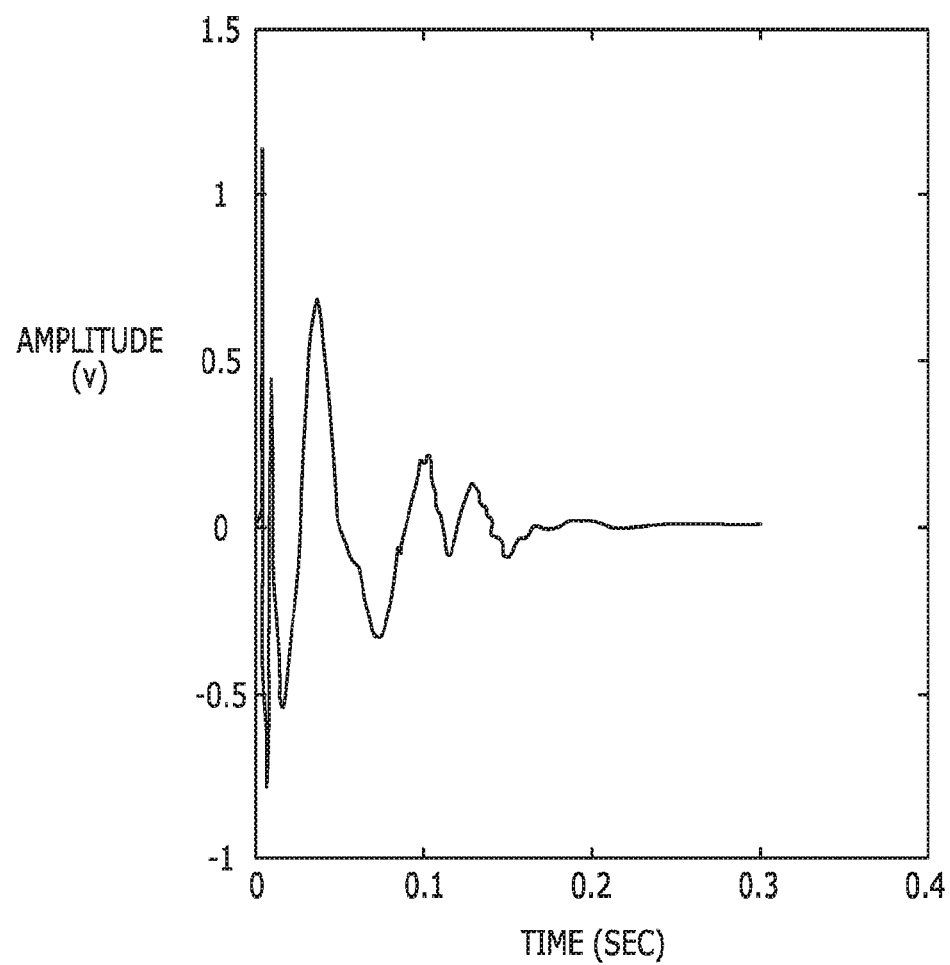
FIG. 7 is a plot of CAP recorded from a rat sciatic nerve with a bipolar nerve cuff with a central reverse window ground contact.

In all animals, very stable sciatic CAPs were observed with proximal stimulation (example shown in FIG. 7). Movement artefacts, previously observed during similar experiments with separate common (ground) electrodes were very well suppressed with this cuff design. CAP records also showed similar features and values over the duration of the experiments for 3 to 4 hours.

VII. Additional Uses of the Modified Nerve Cuff Electrode

Figure 8:
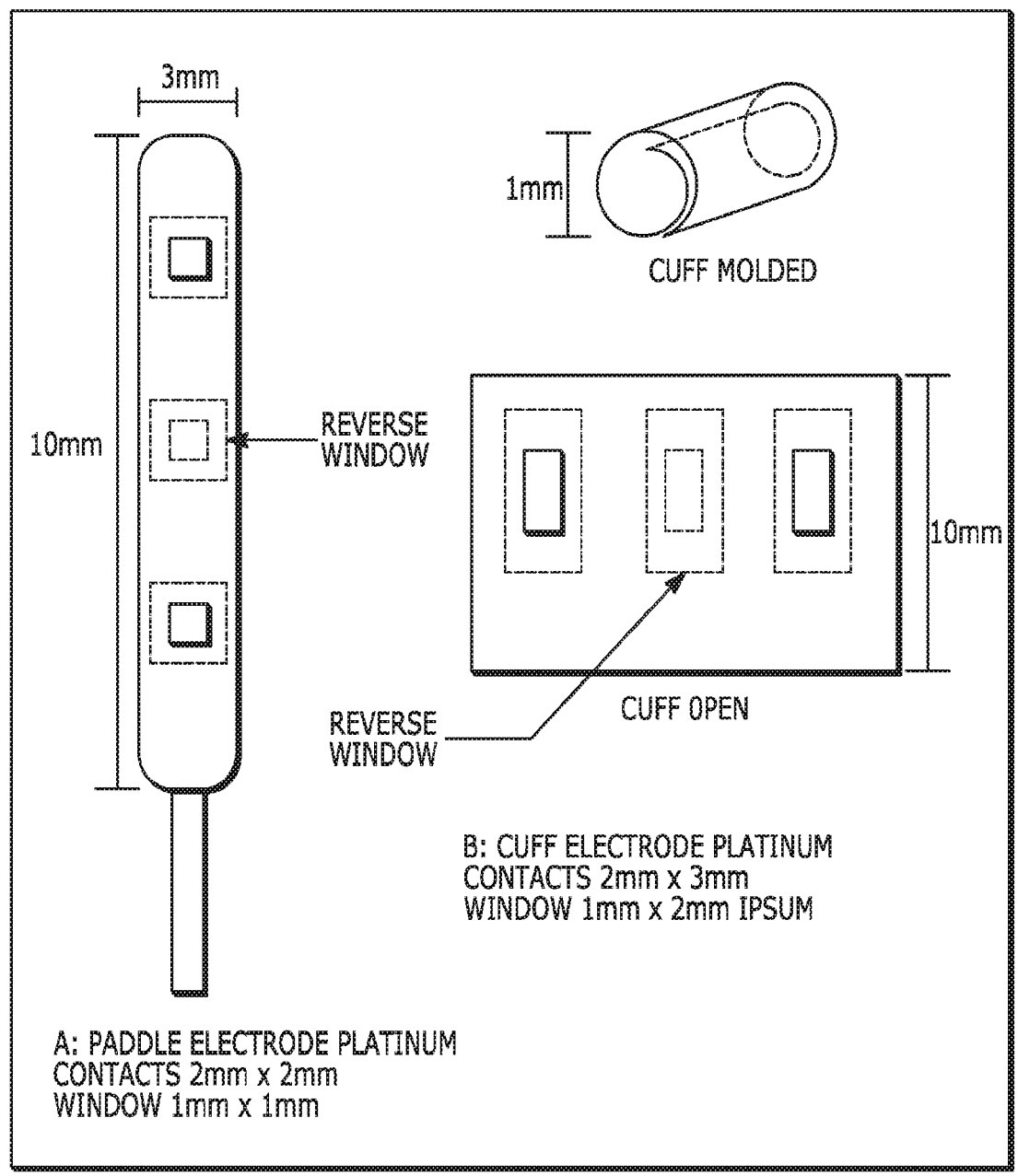
FIG. 8 is another illustration of two different types of electrodes with two flanking contacts and a central reverse facing window.
Figure 9:
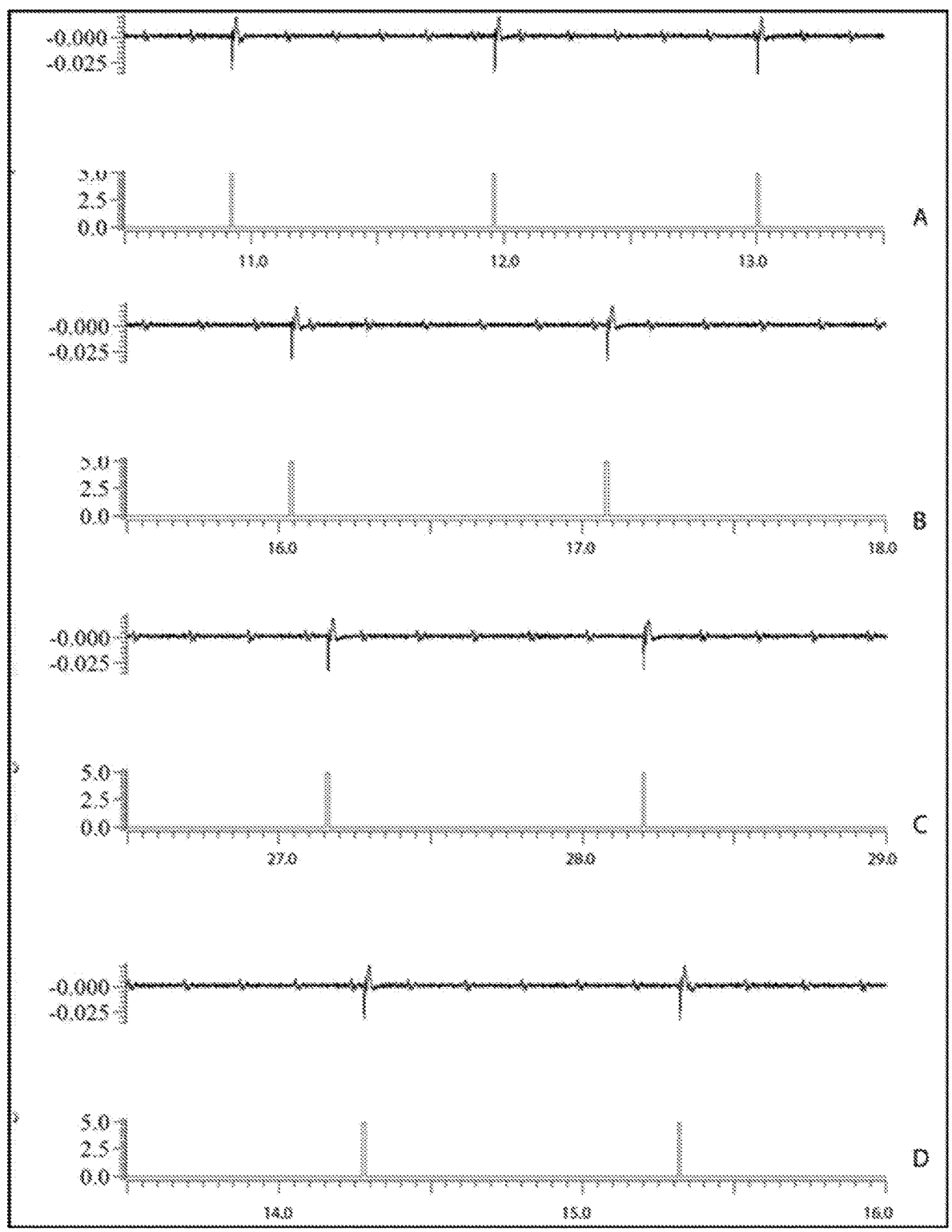
FIG. 9 is a series of recordings of spinal evoked potentials over a time duration spanning 40 minutes showing the stability of neural signals recorded with a bipolar recording electrode with a reverse facing window electrode contact.

Other types of electrodes can be fabricated with the reverse-facing electrode contacts. For example, a paddle electrode (shown in FIG. 8) can be constructed with one or more reverse-facing electrode contacts and one or more electrode contacts on an interior surface of the paddle electrode. The paddle electrode (shown in FIG. 8) can be used for spinal recording and/or stimulation. As shown in FIG. 9, the paddle electrode can take stable recordings of spinal evoked potentials over a time duration spanning 40 minutes.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The invention claimed is:

1. A nerve cuff electrode comprising:
    a plurality of electrode contacts; and
    a nerve cuff comprising:
        a first insulative layer comprising an inner surface configured to face a peripheral nerve; and
        a second insulative layer comprising an outer surface configured to face away from the peripheral nerve, wherein the plurality of electrode contacts are positioned between the first insulative layer and the second insulative layer,
    wherein the first insulative layer comprises at least one window configured to face the peripheral nerve and to electrically expose an active surface of at least one of the plurality of electrode contacts to the peripheral nerve such that the at least one of the plurality of electrode contacts is in electrical communication with the peripheral nerve,
    wherein the second insulative layer comprises at least another window configured to face away from the peripheral nerve and expose an active surface of at least one other of the plurality of electrodes away from the peripheral nerve, and
    wherein the at least one other of the plurality of electrode contacts is electrically isolated from the peripheral nerve by the first insulative layer and the at least one of the plurality of electrode contacts by the second insulative layer and is a stable ground electrode.

2. The nerve cuff electrode of claim 1, wherein
    the at least one of the plurality of electrode contacts having the active surfaces configured to be in electrical communication with the peripheral nerve comprises two or more of the plurality of electrode contacts and are configured for recording activity of the peripheral nerve; and
    the at least one other of the plurality of electrodes having the active surface facing away from the peripheral nerve comprises a single electrode contact.

3. The nerve cuff electrode of claim 2, wherein the single electrode contact is located between the two or more of the plurality of electrode contacts in electrical communication with the peripheral nerve.

4. The nerve cuff electrode of claim 1, wherein the inner surface defines an inner diameter of the nerve cuff that is equal to at least the diameter of the peripheral nerve.

5. The nerve cuff electrode of claim 1, wherein at least one of the plurality of electrode contacts are configured to be placed in electrical contact with a lead wire.

6. The nerve cuff electrode of claim 5, wherein the lead wire is operatively coupled to an external device,
    wherein the external device is configured for recording and/or stimulation.

7. The nerve cuff electrode of claim 1, wherein an active surface of the at least one of the plurality of electrode contacts faces the first insulative layer and an active surface of the other at least one of the plurality of electrode contacts faces the second insulative layer.

8. The nerve cuff electrode of claim 1, wherein the first insulative layer and/or the second insulative layer comprises silicone.

* * * * *